United States Patent [19]
Vogt

[11] Patent Number: 5,412,976
[45] Date of Patent: May 9, 1995

[54] APPARATUS FOR DETERMINING THE AIR PERMEABILITY OF A CLOTH WEB

[75] Inventor: Horst Vogt, Zuerich, Switzerland

[73] Assignee: Textest AG, Zuerich, Switzerland

[21] Appl. No.: 192,012

[22] Filed: Feb. 4, 1994

[30] Foreign Application Priority Data

Feb. 9, 1993 [CH] Switzerland .................. 00389/93

[51] Int. Cl.⁶ .................................. G01N 15/08
[52] U.S. Cl. ............................. 73/38; 73/37.7
[58] Field of Search .......... 73/38, 37.6, 37.7, 37.8

[56] References Cited

U.S. PATENT DOCUMENTS

| | | | |
|---|---|---|---|
| 3,059,466 | 10/1962 | Urmenyi | 73/37.7 |
| 3,115,037 | 12/1963 | Forrester | 73/37.7 X |
| 3,371,518 | 3/1968 | Keyes | 73/38 |
| 3,439,536 | 4/1969 | Cushman | 73/38 X |
| 4,246,775 | 1/1981 | Stultz | 73/38 |
| 4,311,037 | 1/1982 | Gotchel et al. | 73/37.7 X |
| 4,495,796 | 1/1985 | Hester et al. | 73/37.7 X |

*Primary Examiner*—Hezron E. Williams
*Assistant Examiner*—J. David Wiggins
*Attorney, Agent, or Firm*—Flynn, Thiel, Boutell & Tanis

[57] ABSTRACT

For continuous measurement of the air permeability of a moving or stationary cloth web, the latter is guided over a measuring orifice which opens at the end of a measuring tube through a convexly curved outer surface of a measuring head. This convexly curved surface deflects the web. As a result of the tensile stress in the web, the web thereby automatically sealingly clings to this surface around the measuring orifice. In the measuring tube, air is sucked by a pump through the web part extending across the measuring orifice. The flow speed of the air sucked through a test sample is measured in a flowmeter, is indicated as the air permeability of the test sample by an indicator instrument, and if appropriate is used for regulation.

17 Claims, 3 Drawing Sheets

APPARATUS FOR DETERMINING THE AIR PERMEABILITY OF A CLOTH WEB

FIELD OF THE INVENTION

The invention relates to an apparatus for determining the air permeability of a cloth web.

BACKGROUND OF THE INVENTION

Apparatuses of this type are used for the rapid and accurate determination of the air permeability of sheet-like structures of all types in the laboratory or directly during production or treatment of such sheet-like structures, for example textile webs for the production of balloon envelopes, parachutes, and geotextiles, and also wire meshes, etc. Since the air permeability is a measure of the density of a sheet-like structure, the determination of the air permeability can also be used directly for detecting structural changes in the inspected cloth web.

A known apparatus of this generic type includes a measuring head with a cylindrical measuring tube which opens through a surface of the measuring head in order to form a typically circular measuring orifice. The suction side of a pump is connected to the measuring tube. To determine air permeability, a test sample of the cloth web is pressed between the measuring orifice and a pressure ring coordinated with the size of the measuring orifice, and air is sucked by means of the pump through the measuring orifice, the clamped test sample and the pressure ring. The air permeability is the speed of the air flow under a given pressure drop across the test sample. The flow speed of the air sucked through the test sample is measured in a flowmeter, and is indicated as the air permeability of the test sample by an indicator instrument.

However, this known apparatus is designed for measurements on a stationary test sample. It is not suitable for determining the air permeability on a running web. This is because, for this, the measuring head and the pressure ring would have to be moved in synchronism with the running web, because satisfactory sealing around the circumference of the measuring orifice by means of a stationary pressure ring is impossible when a web is running. This would, however, lead to constructions involving a very high cost. On the other hand, a determination of the air permeability on a running web, for example in a treatment installation in which a web is guided continuously in a spread-out state under a regulated tension, would be highly desirable, since stopping of the installation for the purpose of measuring the air permeability could be avoided.

SUMMARY OF THE INVENTION

The invention provides an apparatus which is of the generic type mentioned at the outset, and which, with the simplest possible construction, allows a perfect measurement of the air permeability of a cloth web transported in spread-out form.

As a result of a simple measure, the necessary lateral sealing around the measuring orifice takes place automatically, even when the web is running, so that there is no need for a special pressure ring. By means of the apparatus according to the invention, the air permeability of even a running web can be determined, since it is sufficient to guide at least part of the web width over the measuring head, which can be arranged in a stationary manner at a suitable location along the web path.

The outer surface of the measuring head can have a spherical or semi-cylindrical shape and can be arranged in such a way that it guides the web round on its path over this surface or deflects it out of its transport plane, in order to thereby achieve the sealing around the measuring orifice.

The necessary sealing can be improved even further by providing another hole or the like which opens through the surface and is subject to a vacuum.

It is also possible to determine the air permeability of a web simultaneously at a plurality of locations over the web width.

A constructive simplification of the measuring head is achieved by providing a planar surface portion on the head, and because the test sample extends completely flat across the measuring orifice and air is sucked through over the entire test area of the test sample perpendicular to the latter, measuring accuracy is increased.

BRIEF DESCRIPTION OF THE DRAWINGS

The invention is explained in more detail below by means of exemplary embodiments and with reference to the diagrammatic representations in the drawing, in which.

DETAILED DESCRIPTION

Figure 1:
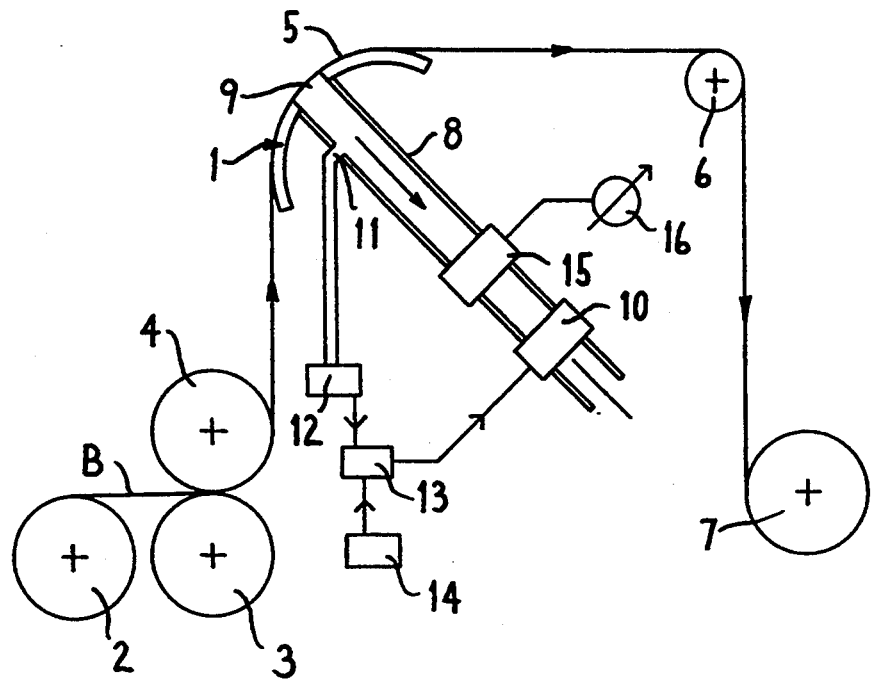
FIG. 1 is a diagrammatic side view of an especially simple embodiment of an apparatus according to the invention and the guidance of a cloth web which is transported in spread-out form before and after this apparatus.

FIG. 1 diagrammatically shows the arrangement of an apparatus for determining air permeability in a calendaring machine. A cloth web B wound on a stock drum 2 is unwound from the latter, is guided between a pair of rollers 3, 4 and is deflected, and then passes over a further deflecting roller 6 and to a winding drum 7, onto which the web B is wound again. Along its entire path from the stock drum 2 to the winding drum 7, the web B is guided in spread-out form and is held in a known way under a regulated tensile stress. Between the deflection caused by the roller 4 of the pair of rollers 3, 4 and the deflection caused by roller 6, the cloth web B is deflected a further time, specifically by an outer surface of a measuring head 5, the surface being convexly curved transversely to the longitudinal axis of the web B, and the measuring head 5 being part of an apparatus, designated in general at 1, for determining the air permeability of the cloth web B. From the side of the measuring head 5 facing away from the web B, a measuring tube 8 opens through the outer surface of the measuring head 5 and forms a measuring orifice 9. When the apparatus 1 is in operation, air is sucked in the direction of the arrow by means of a pump 10 through the part of the cloth web B which covers the measuring orifice 9. The pressure drop across the cloth web B is picked up in the measuring tube 8 at a pressure-measuring point 11 and is fed to a pressure sensor 12 via a conduit. The output signal of the pressure sensor 12 is compared in a variable-gain amplifier or comparator 13 with an adjustable desired value which a desired-value transmitter 14 supplies. The difference signal corresponding to the actual value minus the desired value is fed back to the pump 10, so that the pressure drop across the cloth web B is kept constant at the set desired value.

The flow speed of the air sucked through the part of the web B resting on the measuring orifice is measured in a flowmeter 15, is indicated as the air permeability of the web B on an indicator instrument 16, and if appropriate is used for controlling the installation.

The tensile stress maintained in the running cloth web B ensures at all times that the web B bears closely against the convex outer surface of the measuring head 5 and consequently that there is good sealing between the web B and the convex outer surface all around the measuring orifice 9.

Figure 2:
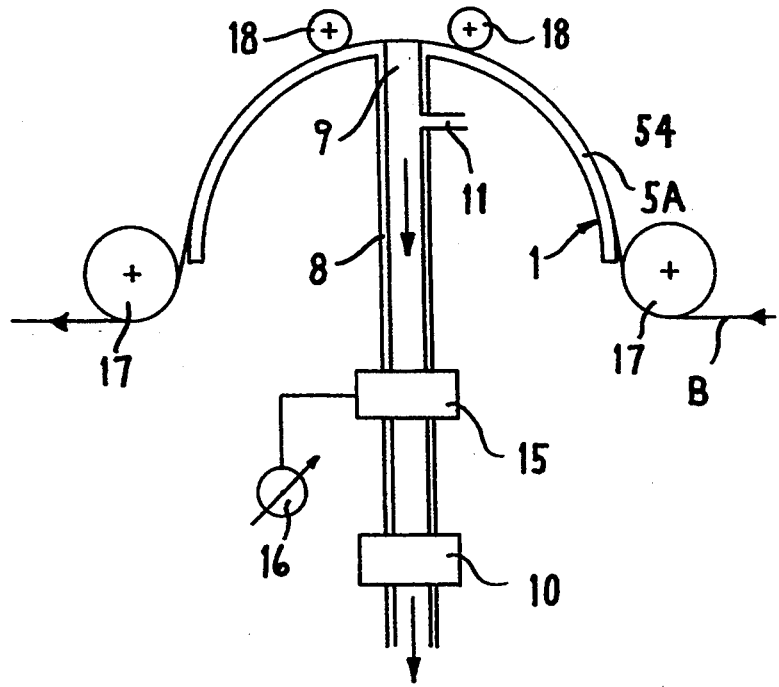
FIG. 2 is a diagrammatic view similar to FIG. 1, but showing a second embodiment of an apparatus according to the invention.

In the exemplary embodiment according to FIG. 2, the cloth web B is guided before and after the measuring head 5A by respective deflecting rollers 17. As a result, for the cloth web B which is otherwise guided flat, a sufficiently large looping deflection of the web B around the measuring head is achieved. The deflecting rollers 17 can be free-running rollers, or rollers driven in the same direction or in opposite directions at the same or differing speeds, in order to vary the tensile stress of the web B and therefore the force with which the web is pressed against the measuring head in order to achieve the necessary sealing. By means of further press rollers 18 which, with respect to the longitudinal direction of the web B, are arranged directly before, after and/or next to the measuring orifice 9, the pressure of the web B against the measuring head can be further increased.

Figure 3:
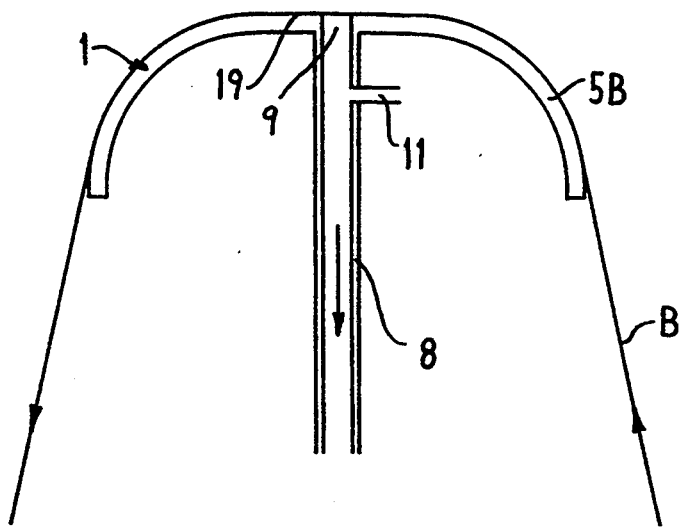
FIG. 3 is a diagrammatic side view of an alternative embodiment of a measuring head of the embodiment of FIG. 1.

In the alternative version illustrated in FIG. 3, the outer surface of the measuring head 5B has, in the region directly adjacent the measuring orifice 9, a planar middle portion 19, as seen in a direction transverse to the longitudinal axis of the web B. A constructive simplification of the measuring head 5B is achieved thereby. Since the cloth web B rests completely flat on the surface portion 19 having measuring crifice 9, the air flows vertically through the web B in the entire region of the measuring orifice, so that the measurement accuracy cannot be distorted by angle errors.

Figure 4:
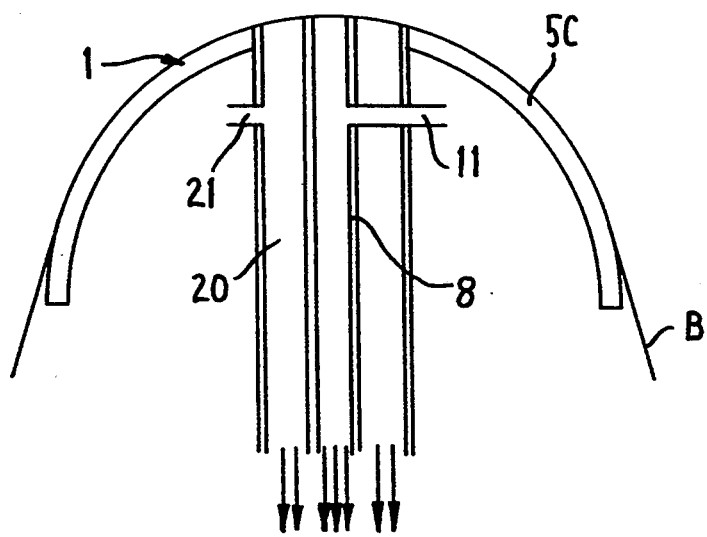
FIG. 4 is a diagrammatic side view similar to FIG. 3, but showing an alternative embodiment of the measuring head of FIG. 3.

In the embodiment according to FIG. 4, the measuring tube 8 is surrounded by an annular channel 20 which extends concentrically thereto and which opens, likewise concentrically to the measuring orifice 9, through the convexly curved outer surface of the measuring head. By means of a second pump not shown here, sufficient air is sucked through this annular channel 20 to ensure that the same vacuum prevails in this annular channel 20 as in the measuring channel 8. This largely prevents the possibility that air will penetrate into the measuring tube 8 from the side and distort the measurement.

Figure 5:
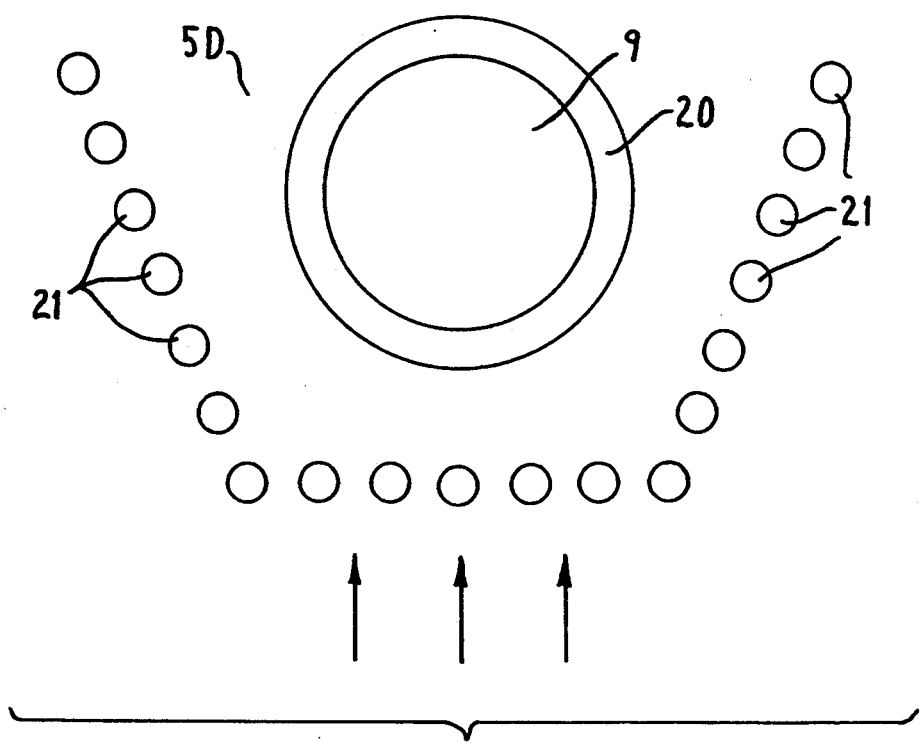
FIG. 5 is a diagrammatic top view of yet another embodiment of the measuring head of FIG. 3.

Finally, FIG. 5 shows in a top view a measuring head 5D which is a development of the embodiment according to FIG. 4. In this version, the apparatus has, in addition to the annular channel 20 surrounding the measuring tube and opening through the outer surface of the measuring head concentrically to the measuring orifice 9, a series of slots or holes 21 which ensure that air accidentally included between the web B and the measuring head 5D can flow off before the web B reaches the measuring orifice 9. In order to improve even further the engagement of the web B against the measuring head 5D, it is possible, by means of a pump or a connection to channel 20, to generate in these bores or slots 21 a vacuum which sucks the web B against the outer surface of the measuring head 5.

All the above-described versions of the apparatus according to the invention can have, in a way not shown in more detail here, and in addition to the determination of the air permeability of the web B, an arrangement for determining the thickness of the web B.

Finally, it is also directly possible to design the apparatus according to the invention in such a way that, in a direction transverse to the web running direction, it has a plurality of measuring arrangements designed identically to one another according to one of the above-described embodiments, in order to simultaneously determine the air permeability of the web B at a plurality of locations spaced along the web width.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an apparatus for determining the air permeability of a sheet-like cloth web held tensioned in spread-out form between rollers, including: a measuring tube opening through an outer surface of a measuring head in order to form a measuring orifice; means for sealing off in an airtight manner, around a circumference of said measuring orifice, a region of the cloth web guided over said measuring orifice; a pump for generating a vacuum in said measuring tube; and means for determining the air quantity sucked through the cloth web; the improvement comprising said surface of said measuring head being convexly curved in the region of said measuring orifice and causing a deflection of the cloth web, through which the latter is automatically pressed sealingly against said surface around said measuring orifice, there being arranged in said measuring head concentrically around said measuring orifice an annular channel having therein during operation the same vacuum as in said measuring tube at said measuring orifice.

2. The apparatus as claimed in claim 1, wherein said outer surface of said measuring head has a spherical or semi-cylindrical shape and is arranged so that it guides the web round on its path over said surface or deflects it out of transport planes thereof.

3. The apparatus as claimed in claim 1, wherein rollers which press the web against said surface of said measuring head are arranged before, next to, and/or after said measuring orifice as seen in the web running direction.

4. The apparatus as claimed in claim 1, wherein there are a plurality of identical measuring arrangements in a direction transverse to the web running direction, in order to determine the air permeability of the web simultaneously at a plurality of locations across the web width.

5. In an apparatus for determining the air permeability of a sheet-like cloth web held tensioned in spread-out form between rollers, including: a measuring tube opening through an outer surface of a measuring head in order to form a measuring orifice; means for sealing off in an airtight manner, around a circumference of said measuring orifice, a region of the cloth web guided over said measuring orifice; a pump for generating a vacuum in said measuring tube; and means for determining the air quantity sucked through the cloth web; the improvement comprising said surface of said measuring head being convexly curved in the region of said measuring orifice and causing a deflection of the cloth web, through which the latter is automatically pressed sealingly against said surface around said measuring orifice, and bores or slots arranged in front of said measuring orifice in the running direction of the web in order to remove air included between the web and said measuring head before measurement.

6. The apparatus as claimed in claim 5, wherein a vacuum, which in addition sucks the web against said surface of said measuring head, prevails in said bores or slots.

7. The apparatus as claimed in claim 5, wherein said outer surface of said measuring head has a spherical or semi-cylindrical shape and is arranged so that it guides the web round on its path over said surface or deflects it out of transport planes thereof.

8. The apparatus as claimed in claim 5, wherein rollers which press the web against said surface of said measuring head are arranged before, next to, and/or after said measuring orifice as seen in the web running direction.

9. The apparatus as claimed in claim 5, wherein there are a plurality of identical measuring arrangements in a direction transverse to the web running direction, in order to determine the air permeability of the web simultaneously at a plurality of locations across the web width.

10. In an apparatus for determining the air permeability of a sheet-like cloth web held tensioned in spread-out form between rollers, including: a measuring tube opening through an outer surface of a measuring head in order to form a measuring orifice; means for sealing off in an airtight manner, around a circumference of said measuring orifice, a region of the cloth web guided over said measuring orifice; a pump for generating a vacuum in said measuring tube; and means for determining the air quantity sucked through the cloth web; the improvement comprising said surface of said measuring head being convexly curved in the region of said measuring orifice and causing a deflection of the cloth web, through which the latter is automatically pressed sealingly against said surface around said measuring orifice, and means incorporated into the measuring head, for measuring the thickness of the web.

11. The apparatus as claimed in claim 10, wherein said outer surface of said measuring head has a spherical or semi-cylindrical shape and is arranged so that it guides the web round on its path over said surface or deflects it out of transport planes thereof.

12. The apparatus as claimed in claim 10, wherein rollers which press the web against said surface of said measuring head are arranged before, next to, and/or after said measuring orifice as seen in the web running direction.

13. The apparatus as claimed in claim 10, wherein there are a plurality of identical measuring arrangements in a direction transverse to the web running direction, in order to determine the air permeability of the web simultaneously at a plurality of locations across the web width.

14. In an apparatus for determining the air permeability of a sheet-like cloth web held tensioned in spread-out form between rollers, including: a measuring tube opening through an outer surface of a measuring head in order to form a measuring orifice; means for sealing off in an airtight manner, around a circumference of said measuring orifice, a region of the cloth web guided over said measuring orifice; a pump for generating a vacuum in said measuring tube; and means for determining the air quantity sucked through the cloth web; the improvement comprising said surface of said measuring head being convexly curved in the region of said measuring orifice and causing a deflection of the cloth web, through which the latter is automatically pressed sealingly against said surface around said measuring orifice, said outer surface of said measuring head being planar in a direction transverse to the longitudinal axis of the web in a region directly adjacent to said measuring orifice.

15. The apparatus as claimed in claim 14, wherein said outer surface of said measuring head has a spherical or semi-cylindrical shape and is arranged so that it guides the web round on its path over said surface or deflects it out of transport planes thereof.

16. The apparatus as claimed in claim 14, wherein rollers which press the web against said surface of said measuring head are arranged before, next to, and/or after said measuring orifice as seen in the web running direction.

17. The apparatus as claimed in claim 14, wherein there are a plurality of identical measuring arrangements in a direction transverse to the web running direction, in order to determine the air permeability of the web simultaneously at a plurality of locations across the web width.

* * * * *